United States Patent [19]

Manning et al.

[11] Patent Number: 4,491,577
[45] Date of Patent: * Jan. 1, 1985

[54] ANTAGONISTS OF THE ANTIDIURETIC ACTION OF ARGININE VASOPRESSIN

[75] Inventors: Maurice Manning, Toledo, Ohio; Wilbur H. Sawyer, Scarsdale, N.Y.

[73] Assignees: The Medical College of Ohio, Toledo, Ohio; The Trustees of Columbia University, New York, N.Y.

[*] Notice: The portion of the term of this patent subsequent to Jan. 4, 2000 has been disclaimed.

[21] Appl. No.: 455,866

[22] Filed: Jan. 5, 1983

Related U.S. Application Data

[63] Continuation-in-part of Ser. No. 322,071, Nov. 16, 1981, Pat. No. 4,399,125.

[51] Int. Cl.$^3$ .................. A61K 37/00; C07C 103/52
[52] U.S. Cl. ............................. 424/177; 260/112.5 R
[58] Field of Search ............... 260/112.5 R; 424/177

[56] References Cited

U.S. PATENT DOCUMENTS 4,367,225  1/1983  Manning et al. ............ 260/112.5 R
4,399,125  8/1983  Manning et al. ............ 260/112.5 R Primary Examiner—Delbert R. Phillips
Attorney, Agent, or Firm—Emch, Schaffer & Schaub

[57] ABSTRACT

Compounds acting as antagonists of the antidiuretic activity of arginine vasopressin are those of the formula

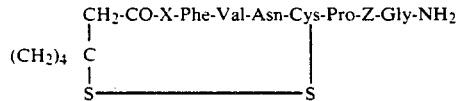

wherein X is (D- or L-)Tyr(R), D-Tyr, D-Phe, D-Val, D-Leu D-Ile, D-Arg, D-Gln, D-Asn, D-NVa, D-Nle, D-Cha, D-Abu, D-Thr or D-Met; R is methyl, ethyl, propyl or butyl and Z is D- or L-Arg. Also acting as antagonists of the antidiuretic action of arginine vasopressin are compounds of the formula

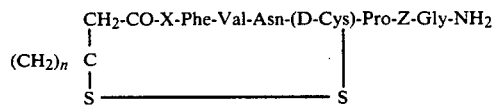

wherein X and Z are as above and n is 4 or 5.

Other antagonists of the antidiuretic action of arginine vasopressin are of the formula

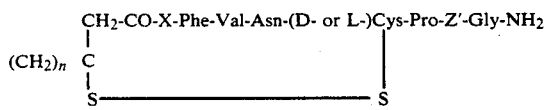

wherein X and n are as above and Z' is (D- or L-)Orn or (D- or L-)Lys.

Other antagonists of the antidiuretic action of arginine vasopressin are of the formula

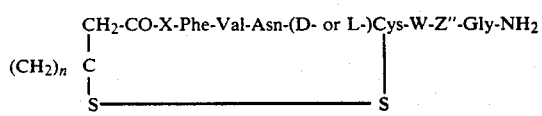

wherein X is above, W is D-Pro, $\Delta^3$-Pro or HO-Pro; Z'' is (D- or L-)Arg, (D- or L-)Lys or (D- or L-)Orn and n is 4 or 5; provided that when X is (D- or L-)Tyr(R) and n is 5, W is HO-Pro or D-Pro and that when X is D-Gln or D-Asn and n is 5, W is also Pro.

32 Claims, No Drawings

ANTAGONISTS OF THE ANTIDIURETIC ACTION OF ARGININE VASOPRESSIN

The invention described herein was made in the course of work under a grant or award from the Department of Health and Human Services.

REFERENCE TO RELATED APPLICATION

This is a continuation-in-part of Manning et al., Ser. No. 322,071, filed Nov. 16, 1981 now U.S. Pat. No. 4,399,125 which issued on Aug. 16, 1983. The term of this patent subsequent to Jan. 4, 2000, has been disclaimed.

BACKGROUND OF THE INVENTION

This invention relates to novel peptides which antagonize the antidiuretic and/or vasopressor action of arginine vasopressin in vivo.

PRIOR ART STATEMENT

Attempts to develop clinically useful synthetic antagonists of in vivo antidiuretic and/or vasopressor responses to arginine vasopressin, the antidiuretic hormone (ADH), have led to the synthesis and pharmacological evaluation of hundreds of analogs of the neurohypophysial peptides, oxytocin and vasopressin.

Analogs which can effectively antogonize the in vivo vasopressor responses to ADH have been reported by Dyckes et al., *J. Med. Chem.*, vol. 17 (1974) at 250; Manning et al., *J. Med. Chem.*, volume 20 (1977) at 1228; Bankowski et al., *J. Med. Chem.*, volume 21 (1978) at 850; Kruszynski et al., *J. Med. Chem.*, volume 23 (1980) at 364 and Lowbridge et al., *J. Med. Chem.*, vol. 21 (1978) at 313, herein incorporated by reference.

Kruszynski et al. reported that [1-(β-mercapto-β,β-cyclopentamethylenepropionic acid), 2-(O-methyl)-tyrosine]-arginine vasopressin and [1-(β-mercapto-β,β-cyclopentamethylenepropionic acid]-arginine vasopressin are potent vasopressor antagonists, which also have very low antidiuretic potency.

Manning et al. (1977) described the synthesis of [1-deaminopenicillamine, 4-valine, 8-D-arginine] vasopressin and Lowbridge et al. the synthesis of [1-(β-mercapto-β,β-cyclopentamethylenepropionic acid), 4-valine, 8-D-arginine] vasopressin. Both of these compounds have reduced antidiuretic activity and are potent antagonists of the vasopressor response to AVP.

Analogs of vasopressin or oxytocin which antagonize antidiuretic responses to ADH have been reported by Chan et al., *Science*, vol. 161 (1968) at 280 and *J. Pharmacol. Exp. Ther.*, vol 174 (1970) at 541 and vol. 196 (1976) at 746; Nestor et al., *J. Med. Chem.*, vol. 18 (1975) at 1022 and Larsson et al., *J. Med. Chem.*, vol. 21 (1978) at 352, herein incorporated by reference. None of the compounds reported has been pharmacologically or clinically useful as an antidiuretic antagonist.

The synthesis and evaluation of vasopressin analogs, incorporating etherified tyrosin at the 2-position, valine at the 4-position and D- or L-arginine at the 8-position, which antagonize the anti-antidiuretic action of ADH in vivo, have been reported by Sawyer et al., *Science*, vol. 212 (1981) at 49 and Manning et al., *J. Med. Chem.*, vol. 24 (1981) at 701, herein incorporated by reference.

Synthetic vasopressins have been disclosed in the following U.S. Pat. Nos. 3,371,080, Boissonas et al.; 3,415,805, Siedel et al.; 3,418,307, Boissonnas et al.; 3,454,549, Boissonnas et al.; 3,497,491, Zaoral; 4,148,787, Mulder et al.

Of these references, Boissonnas et al., U.S. Pat. No. 3,371,080, discloses that 2-phenylalanine-8-ornithine vasopressin has a vasoconstrictive active equal to that of natural vasopressins but low antidiuretic activity. The remaining references disclose synthetic vasopressins having high or relatively specific antidiuretic activity.

Synthetic modifications of oxytocin are disclosed by Manning in U.S. Pat. Nos. 3,691,147 and 3,700,652.

It is therefore apparent that there is a continuing need for the development of pharmacologically and clinically effective antagonists of the antidiuretic action of arginine vasopressin.

OBJECT OF THE INVENTION

It is the object of the invention to provide novel antagonists of the antidiuretic action of ADH, which are effective in vivo.

SUMMARY OF THE INVENTION

This invention relates to novel antagonists of the antidiuretic action of ADH, which are compounds of Formulas I, II, III and IV:

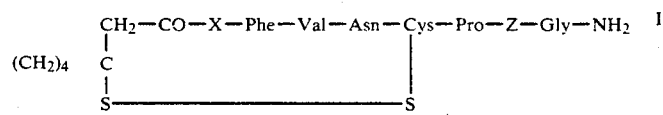

wherein X is (D- or L-)Tyr(R), D-Tyr, D-Phe, D-Val, D-Leu, D-Ile, D-Arg, D-Gln, D-Asn, D-NVa, D-Nle, D-Cha, D-Abu, D-Thr or D-Met; R is methyl, ethyl, propyl or butyl and Z is D- or L-Arg;

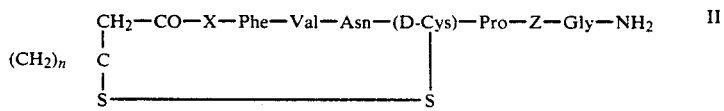

wherein X and Z are as above and n is 4 or 5;

$$(CH_2)_n \begin{matrix} CH_2-CO-X-Phe-Val-Asn-(D\text{- or }L\text{-})Cys-Pro-Z'-Gly-NH_2 \\ | \\ C \\ | \\ S\underline{\hspace{5cm}}S \end{matrix} \quad III$$

wherein X and n are as above; Z' is (D- or L-)Lys or (D- or L-)Orn;

$$(CH_2)_n \begin{matrix} CH_2-CO-X-Phe-Val-Asn-(D\text{- or }L\text{-})Cys-W-Z''-Gly-NH_2 \\ | \\ C \\ | \\ S\underline{\hspace{5cm}}S \end{matrix} \quad IV$$

wherein X and n are as above; W is D-Pro, $\Delta^3$-Pro or HO-Pro; and Z" is (D- or L-)ARg, (D- or L-)Orn or (D- or L-)Lys; provided that, when X is (D- or L-)Tyr(R) and n is 5, W is HO-Pro or D-Pro and that when X is D-Gln or D-Asn, W is also Pro.

This invention further relates to a method for antagonizing the in vivo response to ADH, comprising administering to an animal being treated an amount of one of the foregoing compounds, in admixture with a physiologically and pharamceutically acceptable carrier, effective to antagonize the antidiuretic response to ADH.

DETAILED DESCRIPTION

Compounds of the invention are derivatives of arginine vasopressin. In the specification and claims, "Cy" and "Cys" are used interchangeably. Amino acids are in the L-form, unless otherwise indicated. The correlation between full names and abbreviations is:

dAVP, 1-deamino-arginine-vasopressin;

dPAVP, [1-deaminopenicillamine]-arginine vasopressin;

$d(CH_2)_5AVP$, [1-($\beta$-mercapto-$\beta$,$\beta$-cyclopentamethylenepropionic acid)]-arginine vasopressin;

dVDAVP, 1-deamino-[4-valine, 8-D-arginine] vasopressin;

dPVDAVP, [1-deaminopenicillamine, 4-valine, 8-D-arginine] vasopressin;

$d(CH_2)_5VDAVP$, [1-($\beta$-mercapto-$\beta$,$\beta$-cyclopentamethylenepropionic acid), 4-valine, 8-D-arginine] vasopressin;

$d(CH_2)_5$ Tyr(Me)VDAVP, [1-($\beta$-mercapto-$\beta$,$\beta$-cyclopentamethylenepropionic acid, 2-O-methyltyrosin, 4-valine, 8-D-arginine] vasopressin;

$d(CH_2)_5$-D-Tyr-VDAVP, [1-($\beta$-mercapto-$\beta$,$\beta$-cyclopentamethylenepropionic acid), 2-D-tyrosine, 4-valine, 8-D-arginine] vasopressin;

$d(CH_2)_5$-D-TyrVAVP, [1-($\beta$-mercapto-$\beta$,$\beta$-cyclopentamethylenepropionic acid), 2-D-tyrosine, 4-valine]-arginine vasopressin;

$d(CH_2)_4(Tyr(Et)VAVP$, [1-($\beta$-mercapto-$\beta$,$\beta$-cyclotetramethylenepropionic acid), 2-O-ethyltyrosin, 4-valine]-arginine vasopressin;

$(CH_2)_4)Tyr(Et)VDAVP$, [1-($\beta$-mercapto-$\beta$,$\beta$-cyclotetramethylenepropionic acid), 2-O-ethyltyrosin, 4-valine, 8-D-arginine] vasopressin;

$d(CH_2)_4D$-Tyr(Et)VAVP, [1-($\beta$mercapto-$\beta$,$\beta$-cyclotetramethylenepropionic acid), 2-D-(O-ethyl)-tyrosin, 4-valine]-arginine vasopressin;

$d(CH_2)_4$-D-Tyr(Et)VDAVP, [1-($\beta$-mercapto-$\beta$,$\beta$-cyclotetramethylenepropionic acid), 2-D-(O-ethyl)-tyrosin, 4-valine, 8-D-arginine] vasopressin;

$d(CH_2)_5D$-Phe$^2$-D-Cys$^6$VAVP, [1-($\beta$-mercapto-$\beta$,$\beta$-cyclopentamethylenepropionic acid), 2-D-phenylalanine, 4-valine, 6-D-cysteine]-arginine vasopressin;

$d(CH_2)_5[Tyr(Et)^2]D$-Cys$^6$VAVP, [1-($\beta$-mercapto-$\beta$,$\beta$-cyclopentamethylenepropionic acid), 2-O-ethyltyrosin, 4-valine, 6-D-cysteine]-arginine vasopressin;

$d(CH_2)_5[D-Tyr(Et)^2]D$-Cys$^6$VAVP, [1-($\beta$-mercapto-$\beta$,$\beta$-cyclopentamethylenepropionic acid), 2-D-(O-ethyl)-tyrosine, 4-valine, 6-D-cysteine]-arginine vasopressin;

$d(CH_2)_5$-D-Tyr(Et)VLVP, [1-($\beta$-mercapto-$\beta$,$\beta$-cyclopentamethylenepropionic acid), 2-D-(O-ethyl)-tyrosin, 4-valine]-lysine vasopressin;

$d(CH_2)_5Tyr(Et)VLVP$, [1-($\beta$-mercapto-$\beta$,$\beta$-cyclopentamethylenepropionic acid), 2-O-ethyltyrosine, 4-valine]-lysine vasopressin;

$d(CH_2)_5$-D-Ile$^2$Val$^4$Orn$^8$VP, [1-($\beta$-mercapto-$\beta$,$\beta$-cyclopentamethylenepropionic acid), 2-D-isoleucine, 4-valine]-ornithine vasopressin;

$d(CH_2)_5$-D-Tyr(Et)-D-Pro$^7$VAVP, [1-($\beta$-mercapto-$\beta$,$\beta$-cyclopentamethylenepropionic acid), 2-D-(O-ethyl)tyrosine, 4-valine, 7-D-proline]-arginine vasopressin and $d(CH_2)_5Tyr(Et)$-D-Pro$^7$VAVP, [1-($\beta$-mercapto-$\beta$,$\beta$-cyclopentamethylenepropionic acid), 2-O-ethyltyrosine, 4-valine, 7-D-proline]-arginine vasopressin.

The active peptides were synthesized by solid phase synthesis, as described by Bankowski et al. (1978), supra; Merrifield, *J. Am. Chem. Soc.*, vol. 85 (1963) at 2149 and *Biochemistry*, vol. 3 (1964) at 1385; Manning, *J. Am. Chem. Soc.*, vol. 90 (1968) at 1348; Manning et al., *J. Med. Chem.*, vol. 19 (1976) at 376; Lowbridge et al., *J. Med. Chem.*, vol. 20 (1977) at 1173; Manning et al., *J. Med. Chem.*, vol. 16 (1973) at 975; Kruszynski et al. (1980), supra; Sawyer et al., (1981); supra or Manning et al. (1981), supra.

Initial attempts to design an antagonist of the antidiuretic response to arginine vasopressin (AVP) included synthesis of [1-deaminopenillamine, 4-valine, 8-D-arginine] vasopressin (dPVDAVP) by Manning et al. (1977), supra, and of [1-($\beta$-mercapto-$\beta$,$\beta$-cyclopentamethylenepropionic acid), 4-valine, 8-D-arginine] vasopressin, ($d(CH_2)_5VDAVP$), Lowbridge (1978), supra. These analogs were designed by replacing the two hydrogens on the $\beta$-carbon at the 1-position of the highly active and selective antidiuretic peptide 1-deamino-[4-valine, 8-D-arginine] vasopressin (dVDAVP), Manning et al., *J. Med. Chem.*, vol. 16 (1973) at 975, by two methylene groups and a cyclopentamethylene group, respectively. These substituents had previously been shown to convert the highly potent oxytocic agonist 1-deamino-oxytocin (dOT) into potent antagonists of the oxytocic response to oxytocin, specifically, [1-deaminopenicillamine] oxytocin (dPOT) and [1-($\beta$-mercapto-$\beta$,$\beta$-cyclopentamethylenepropionic acid)] oxytocin, d(CH$_2$)$_5$ OT. See, Hope et al., *J. Biol. Chem.*, vol. 237 (1962) at 1563; Schulz et al., *J. Med. Chem.*, vol. 9, (1966) at 647 and Nestor et al., *J. Med. Chem.*, vol. 18 (1975) at 284.

The discovery of the antidiuretic antagonists d(CH$_2$)$_5$Tyr(alk)VAVP, Sawyer et al. (1981), supra, Manning et al., (1981), supra, led to the synthesis of analogs having a cyclotetramethylene ring at the 1-position. It was found, in accordance with the present invention that the cyclotetramethylene analogs are comparable in activity to the corresponding 2-O-alkyltyrosine-β,β-cyclopentamethylene analogs.

Tyrosine ethers within the scope of this invention include the various isomeric 1–4 carbon alkyl ethers, including propyl, isopropyl and various butyl isomers. Preferred compounds of the invention are Tyr(Et) ethers, particularly D-Tyr(Et) compounds of Formulas I, II, III and IV, wherein Z, Z' or Z" is (D- or L-)Arg, (D- or L-)Lys or (D- or L-)Orn.

Preferred compounds of Formula I are those wherein:
(a) X is (D- or L-)-Tyr(R);
(b) X is D-Tyr(R);
(c) R is ethyl, including each of (a)–(b);
(d) Z is Arg, including each of (a)–(c) and
(e) Z is D-Arg, including each of (a)–(c).

Preferred compounds of Formula II are those wherein:
(a) X is Tyr(R);
(b) X is D-Tyr(R);
(c) R is ethyl, including each of (a)–(b);
(d) X is D-Phe;
(e) Z is Arg, including each of (a)–(d) and
(f) n is 5, including each of (a)–(e).

Preferred compounds of Formula III are those wherein:
(a) X is (D- or L-)Tyr(R);
(b) X is (D- or L-)Tyr(Et);
(c) X is D-Ile;
(d) n is 5, including each of (a)–(c);
(e) Z' is Orn, including each of (a)–(d) and
(f) Z' is Lys, including each of (a)–(d).

Preferred compounds of Formula IV are those wherein:
(a) X is (D- or L-)Tyr(R);
(b) X is (D- or L-)Tyr(Et);
(c) Y is D-Pro, including each of (a)–(b);
(d) n is 5, including each of (a)–(c) and
(e) Z" is Arg, including each of (a)–(d).

The compounds of this invention are accordingly very effective antagonists of the antidiuretic response to ADH. They can therefore be used in pharmacological studies on the contribution of ADH to a variety of pathological logical states involving water retention. It is further contemplated that they could be effective and specific agents for treating the syndrome of inappropriate secretion of ADH, that is, the Schwartz-Bartter syndrome or SIADH. This syndrome can complicate a number of disorders, including carcinomas, pulmonary diseases, intracranial diseases and head injuries, Bartter et. al., *Am. J. Med.*, vol. 42 (1967) at 790.

The compounds of this invention can be employed in mixtures with conventional excipients, i.e., physiologically and pharmaceutically acceptable organic or inorganic carriers suitable for parenteral or other application, provided that the carriers do not interact deleteriously with the active compounds.

Suitable pharmaceutically acceptable carriers include, but are not limited to, water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxymethyl cellulose, polyvinyl pyrrolidone, etc. The pharmaceutical preparations can be sterilized and, if desired, mixed with auxiliary agents, e.g., lubricants, preservatives, stabilizers, wetting agents, emulsifiers, salts for influencing the osmotic pressure, buffers, coloring, flavoring and/or aromatic substances, which do not deleteriously interact with the active compounds.

For parenteral or intranasal application, solutions, preferably aqueous solutions, as well as suspensions, emulsions or implants, including suppositories, are particularly suitable. Ampoules are convenient unit dosages.

The compounds of this invention are generally administered to animals, including but not limited to mammals, e.g, livestock, household pets, humans, cattle, cats and dogs. A diuretically effective daily dosage of the active compounds can be administered parenterally in a single dosage or as divided dosages throughout the day.

Parenteral or intranasal administration is preferred. The compounds of this invention are particularly valuable in the treatment of humans afflicted with water retention of any etiology. In this regard, they can be administered in substantially the same manner as the known compounds oxytocin and vasopressin, to achieve their physiological effects.

It will be appreciated that the actual preferred amounts of active compounds used will vary according to the specific compound being utilized, the particular compositions formulated, the mode of application, and the particular organisms being treated. Optimal application rates under/in a given set of conditions can be ascertained by those skilled in the art of using conventional dosage determination tests in view of the above guidelines.

DESCRIPTION OF PREFERRED EMBODIMENT

Preferred antidiuretic antagonists of this invention are those of Formula I wherein X is D-(O-ethyl)tyrosine and Z is D- or L-arginine.

Without further elaboration, it is believed that one skilled in the art can, using the preceding description, utilize the present invention to its fullest extent. The following specific embodiments are, therefore, to be construed as merely illustrative and not limitative of the remainder of the disclosure in any way whatsoever. In the following Examples, the temperatures are set forth uncorrected in degrees Celsius. Unless otherwise indicated, all parts and percentages are by weight.

Chloromethylated resin (Bio-Rad Bio-Beads SX-1) was esterified by the procedure of Gisin, *Helv, Chim. Acta.*, vol. 56 (1973) at 1476 with Boc-Gly until 0.47 mmol./g. and ~0.64 mmol/g were incorporated. Amino acid derivatives, including Boc-Tyr(Me) (R$_f$(A) 0.7, R$_f$(B)0.8) were supplied by Bachem or synthesized.

Triethylamine (TEA) and N-methylmorpholine (NMM) were distilled from ninhydrin.

Acetic acid used as the HCl-acetic acid cleavage reagent was heated under reflux with boron triacetate and distilled from the reagent. Dimethylformamide (DMF) was distilled under reduced pressure immediately before use. Methanol was dried with magnesium methoxide and distilled. Other solvents and reagents were analytical grade.

Thin layer chromatography (TLC) was done on silica gel plates (0.25 mm, Brinkmann Silplate) using the following solvent systems: A. cyclohexane-chloroform-acetic acid (2:8:1 v/v); B. propan-1-ol-ammonia (34%) (2:1 v/v); C. ethanol (95%)-ammonia (34%) (3:1 v/v); D. chloroform-methanol (7:3 v/v); E. butan-1-ol-acetic acid-water (4:1:5 v/v, upper phase); F, butan-1-ol-acetic acid-water-pyridine (15:3:3:10 v/v). The applied loadings were 10–50 μg. The minimum length of the chromatographs was 10 cm. Chloroplatinate reagent and iodine vapor were used for development of the chromatograms.

Amino acid analysis of the peptides was done by the method of Spackman et al., *Anal. Chem.*, vol. 30 (1958) at 1190, in which peptide samples weighing about 0.5 mg were hydrolyzed with constant boiling hydrochloric acid (400 μl) in evacuated and sealed ampoules for 18 h at 120° C. The analyses were performed using a Beckman Automatic Amino Acid Analyzer, Model 121. Molar ratios were referred to Gly=1.00. Elemental analyses were performed by Galbraith Laboratories, Inc., Knoxville, Tenn. The analytical results for the elements indicated by their respective symbols were within ±0.4% of theoretical values. Optical rotations were measured with a Bellingham Stanley, Ltd., Model A polarimeter, type pl.

EXAMPLE 1

β-(S-Benzylmercapto)-β,β-cyclopentamethylenepropionyl-Try(Me)-Phe-Gln-Asn-Cys(Bzl)-Pro-Arg(Tos)-Gly-NH$_2$ (a) Combination of Solid Phase and Solution Methods.

Boc-Tyr(Me)-Phe-Gln-Asn-Cys(Bzl)-Pro-Arg(Tos)-Gly-NH$_2$, prepared by the method of Bankowski et al., *J. Med. Chem.*, vol. 21 (1978) at 850 (319 mg, 0.26 mmol), was dissolved in CF$_3$COOH (6.5 ml) and stirred at room temperature for 40 mins. Cold ether (20 ml) was added to produce a precipitate, which was filtered and washed with ether (5×10 ml). The product was dried in vacuo over sodium hydroxide pellets. This material (318.5 mg) was dissolved in DMF (0.8 ml), to which was added N-methylmorpholine (10 μl). The resulting solution had a pH of 7–8, measured with moist pH paper. After this neutralized solution was stirred at room temperature for 30 mins, a solution of p-nitrophenyl β-(S-benzylmercapto)-β,β-cyclopentamethylenepropionate, Nestor et al., *J. Med. Chem.*, vol. 18 (1975) at 284, (445 mg, 1.155 mmol in 0.4 ml of DMF) was added. The reaction mixture was stirred at room temperature. After 72 hours' stirring, TLC analysis using system D showed that the reaction mixture stilled contained a trace of the free octapeptide amide. N-Hydroxybenzotriazole monohydrate, Konig et al., *Chem. Ber.*, vol. 103 (1970) at 788, (39.3 mg, 0.26 mmol) was added. Coupling was complete within 5 hours. The precipitate was filtered, washed with cold ethyl acetate (4×10 ml) and dried in vacuo. The crude product (339 mg) was twice reprecipitated from DMF-methanol to give the acylpeptide amide (295.2 mg, 77.3%): mp 209°–211° C., [α]$_D^{24}$= −43.6° (c 0.5, DMF); R$_f$(E) 0.45, R$_f$(F) 0.63 Anal. (C$_{73}$H$_{94}$O$_{14}$N$_{14}$S$_3$) C, H, N.

(b) Total Synthesis on Resin.

Boc-Tyr(Me)-Phe-Gln-Asn-Cys(Bzl)-Pro-Arg(Tos)-Gly-resin (1.11 g, 0.4 mmol prepared from Boc-Gly-resin using solid phase methodology) was converted to the acyloctapeptide resin (1.167 g, weight gain 57 mg, 97.6% of theory) in one cycle of deprotection, neutralization and coupling with p-nitrophenyl β-(S-benzylmercapto)-β,β-cyclopentamethylenepropionate, see Nestor, supra. The resin was ammonolyzed, Manning, *J. Am. Chem. Soc.*, vol.90 (1968) at 1348. The product was extracted with DMF. After the solvent was evaporated in vacuo, the residue was precipitated by addition of water. The crude product (410 mg) was twice reprecipitated from DMF-ethanol to give the acyloctapeptide (302 mg, 50.7% based upon initial glycine content of the resin); mp 206°–208° C. (decomp); R$_f$(E) 0.45; R$_f$(F) 0.63; [α]$_D^{24}$= −43.1° (c 1, DMF). Anal. (C$_{73}$H$_{94}$N$_{14}$O$_{14}$S$_3$) C, H, N.

Amino acid analysis: Tyr, 0.79; Phe, 1.01; Glu, 1.03; Asp, 1.04; Cys(Bzl), 0.97; Pro, 1.03; Arg, 0.99; Gly, 1.00; NH$_3$, 2.95.

EXAMPLE 2

β-(S-Benzylmercapto)-β,β-cyclopentamethylenepropionyl-Tyr(Bzl)-Phe-Gln-Asn-Cys(Bzl)-Pro-Arg(Tos)-Gly-NH$_2$ Boc-Tyr(Bzl)-Phe-Gln-Asn-Cys(Bzl)-Pro-Arg(Tos)-Gly-resin (1.46 g, 0.5 mmol) was converted to the acyloctapeptide resin (1.55 g, weight gain 70 mg, 95.9% of theory) as in Example 1 by one cycle of deprotection, neutralization and coupling with p-nitrophenyl β-(S-benzylmercapto)-β,β-cyclopentamethylenepropionate. The product obtained by ammonolysis of the resin was extracted with DMF. The solvent was evaporated in vacuo and the residue was precipitated by addition of water. The crude product (723 mg) was reprecipitated from DMF-ethanol and DMF-2% aqueous AcOH. Yield: 488 mg (62.4% based on initial Gly content on the resin); mp. 183°–185° C.; R$_f$(E) 0.38; R$_f$(D) 0.41; [α]$_D^{23}$= −23.9° (c, 1, DMF). Anal. (C$_{79}$H$_{98}$N$_{14}$O$_{14}$S$_3$) C, H, N.

Amino acid analysis: Tyr, 0.97; Phe, 1.02; Glu, 1.05; Asp, 1.01; Cys(Bzl), 0.98; Pro, 1.04; Arg, 0.98; Gly, 1.00; NH$_3$.

EXAMPLE 3

[1-(β-Mercapto-β,β-cyclopentamethylenepropionic acid), 2-(O-methyl)tyrosine]-arginine vasopressin (a) From Nonapeptide Amide A solution of the protected nonapeptide amide, prepared as in Example 1, (170 mg, 0.114 mmol) in 400 ml of ammonia (dried over sodium and redistilled) was stirred at the boiling point with sodium from a stick of the metal, contained in a small bore glass tube until a light blue color persisted in the solution for 30 sec, in accordance with duVigneaud, *J. Am. Chem. Soc.*, vol. 76 (1954) at 3115. Dry glacial acetic acid (0.4 ml) was added to discharge the color. The solution was evaporated. A solution of the residue in aqueous acetic acid (0.2%, 800 ml), was treated with 2M ammonium hydroxide solution to give a solution of pH 7.5. To this stirred solution was added gradually an excess of a solution of potassium ferricyanide (0.01M, 11.4 ml), Hope et al., *J. Biol. Chem.*, vol. 237 (1962) at 1563. The yellow solution was stirred for 90 min more and for 1 h with anion-exchange resin (BioRad AG-3, Cl$^-$ form, 10 g damp weight). The suspension was filtered slowly through a bed of resin (80 g damp weight). The resin bed was washed with 300 ml of aqueous acetic acid and the combined filtrate and washings were lyophilized.

The resulting powder (1386 mg) was desalted on a Sephadex G-15 column (110×2.7 cm) and eluted with aqueous acetic acid (50%) at a flow rate of 4 ml/h by the technique of Manning et al., *J. Chromatog.*, vol. 38 (1968) at 396. The eluate was fractionated and monitored for absorbance at 280 nm. The fractions comprising the major peak were pooled and lyophilized. The residue (55.5 mg) was further subjected to gel filtration on a Sephadex G-15 column (100×1.5 cm) and eluted with aqueous acetic acid (0.2M) at a flow rate of 2.5 ml/h. The peptide was eluted in a single peak (absorbance 280 nm). Lyophilization of the pertinent fractions yielded the vasopressin analog (49 mg, 37.3%); $R_f(E)$ 0.19; $R_f(F)$ 0.30; $[\alpha]_D^{22} = -59.6°$ (c 0.19, 1M AcOH).

Amino acid analysis: Tyr 0.81; Phe, 1.01; Glu, 1.04; Asp, 0.98; Pro, 1.04; Arg, 0.95; Gly, 1.00; $NH_3$ 3.10. Analysis following performic acid oxidation prior to hydrolysis according to Moore, *J. Biol. Chem.*, vol. 238 (1963) at 235, gave a $Cys(O_3H)$-Gly ratio of 1.03:1.00.

(b) From Acyloctapeptide.

Treatment of the acyloctapeptide (160 mg, 0.107 mmol) as described in Example 3(a) yielded the analog (64 mg, 51.7%), which was indistinguishable from the foregoing preparation by TLC: $[\alpha]_D^{23} = -59.1°$ (c 0.5, 1M AcOH).

Amino acid analysis: Tyr, 0.80; Phe, 1.02; Glu, 1.02; Asp, 0.98; Pro, 1.03; Arg, 0.96; Gly, 1.00; $NH_3$, 3.05. Analysis following performic acid oxidation prior to hydrolysis gave a $Cys$-$(O_3H)$-Gly ratio of 1.02:1.00.

EXAMPLE 4

[1-(β-Mercapto-β,β-cyclotetramethylenepropionic acid), 2-O-alkyltyrosine, 4-valine]-(L- or D-)-arginine vasopressin Compounds of this series were prepared as in Examples 1-3, to obtain protected intermediates for each analog. The procedures of Bodanszky et al., *J. Am. Chem. Soc.*, vol. 81 (1959) at 5688 and *J. Org. Chem.*, vol. 39 (1974) at 444, employing a p-nitrophenyl ester, facilitated by the use of hydroxybenzotriazole (Konig et al., supra), were used for the coupling of β-(S-benzylmercapto)-β,β-cyclotetramethylenepropionate in accordance with Nestor, supra. The cyclotetramethylene propionate was synthesized by using cyclopentanone. The product melted at 66°-67° C. and, by thin layer chromatography (benzene/acetone) had $R_f$ 0.91.

Each precursor was deblocked with sodium in liquid ammonia to produce a sulfhydryl compound. The latter compounds were oxidatively cyclized with potassium ferricyanide as in the preceding Examples. The analogs were desalted and purified by gel filtration on Sephadex G-15 by a two-step procedure using 50% acetic acid and 0.2M acetic acid, respectively, as eluants. The purity and identity of each analog was ascertained by thin layer chromatography in two different solvent systems, Kruszynski et al., supra.

Results were:

(a) d(CH₂)₄Tyr(Et)VAVP
$R_f(E)$: 0.20
$R_f(F)$: 0.45

(b) d(CH₂)₄Tyr(Et)VDAVP
$R_f(E)$: 0.13
$R_f(F)$: 0.47

(c) d(CH₂)₄-D-Tyr(Et)VAVP
$R_f(E)$: 0.33
$R_f(F)$: 0.55

(d) d(CH₂)₄-D-Tyr(Et)VDAVP
$R_f(E)$: 0.15
$R_f(F)$: 0.77

EXAMPLE 5 cl

[1-(β-Mercapto-β,β-cyclopentamethylenepropionic acid), 2-substituted, 4-valine, 6-D-cysteine]-arginine vasopressin The compounds of this series were made as in Examples 1-4, using the indicated substituents at the 2-position and D-cysteine at the 6-position. The compounds were characterized as in the foregoing Examples. Results were:

| X | $R_f(E)$ | $R_f(F)$ |
|---|---|---|
| D-Phe | 0.20 | 0.65 |
| Tyr(Et) | 0.26 | 0.70 |
| D-Tyr(Et) | 0.15 | 0.64 |

EXAMPLE 6

Antagonism to the vasopressor response was estimated in accordance with Dyckes et al., *J. Med. Chem.*, vol. 17 (1974) at 969. The values are expressed as $pA_2$ values, defined as in Schild et al., *Br. J. Pharmacol.*, vol. 2 (1947) at 189.

Activity as antidiuretic agonists was determined by intravenous injection of the compounds being evaluated in ethanol-anesthesized water-loaded rats in accordance with Sawyer, *Endocrinology*, vol. 63 (1958) at 694. Antagonism of the antidiuretic response to subsequent injections of vasopressin was tested as described by Sawyer et al., *Science*, vol. 212 (1981) at 49.

Antagonistic potencies were determined and expressed as "effective doses" and $pA_2$ values. The "effective dose" is defined as the dose (in nanomoles per kilogram) that reduces the response seen from 2x units of agonist injected 20 min after the dose of antagonist to the response with 1x units of agonist. Estimated in vivo "$pA_2$" values represent the negative logarithms of the effective doses, divided by the estimated volume of distribution (67 ml/kg). Results are given in Table 1.

EXAMPLE 7

[1-(β-Mercapto-β,β-cyclopentamethylenepropionic acid), 2-substituted, 4-valine, 8-substituted vasopressin Representative compounds of this series, of the formula d(CH₂)₅-X²-Z⁸-VAVP, were prepared as in foregoing examples, except that amino acids, other than (D- or L-)arginine, were used as substituents at the 8-position. Physical properties of the compounds were:

| $X^2$ | $Z^8$ | $R_f(E)$ | $R_f(F)$ |
|---|---|---|---|
| Tyr(Et) | Lys | 0.20 | 0.47 |
| Tyr(Et) | Cit | 0.28 | 0.67 |
| D-Tyr(Et) | Lys | 0.16 | 0.65 |
| D-Tyr(Et) | Cit | 0.23 | 0.62 |
| D-Ile | Orn | 0.07 | 0.32 |
| D-Ile | Gln | 0.20 | 0.57 |
| D-Ile | Leu | 0.47 | 0.78 |

Pharmacological properties were evaluated as in Example 6, with the following results:

| $X^2$ | $Z^8$ | ED's in nmoles/kg | |
|---|---|---|---|
| | | Anti-ADH | Anti-VP |
| Tyr(Et) | Lys | 3.9 ± 0.7 | 0.67 ± 0.09 |
| Tyr(Et) | Cit | >390 | 1.9 ± 0.5 |
| D-Tyr(Et) | Lys | 1.5 ± 0.4 | 0.48 ± 0.08 |
| D-Tyr(Et) | Cit | 23 ± 6 | 0.81 ± 0.11 |
| D-Ile | Orn | 1.5 ± 0.2 | 16 ± 2 |
| D-Ile | Gln | ~200 | 31 ± 4 |
| D-Ile | Leu | >25 | >40 |

These experiments show that VAVP derivatives, having Lys or Orn at the 8-position, act as powerful antagonists of the antidiuretic action of arginine vasopressin.

TABLE 1

| Compound | Anti-Antidiuretic | | Antivasopressor | |
|---|---|---|---|---|
| | ED nmoles/Kg | $pA_2$ | ED nmoles/Kg | $pA_2$ |
| $d(CH_2)_5$—D-TyrVAVP | 2.2 ± 0.2 | 7.51 ± 0.08 (4) | 0.29 ± 0.09 | 8.41 ± 0.11 (4) |
| $d(CH_2)_5$Tyr(Me)VDAVP | 15 ± 3 | 6.68 ± 0.11 (4) | 0.28 ± 0.05 | 8.44 ± 0.07 (8) |
| $d(CH_2)_5$Tyr(Et)VDAVP | 5.7 ± 0.5 | 7.10 ± 0.08 (4) | 0.34 ± 0.04 | 8.31 ± 0.05 (8) |
| $d(CH_2)_5$—D-Tyr(Me)VAVP | 1.2 ± 0.3 | 7.77 ± 0.07 (6) | 0.23 ± 0.04 | 8.48 ± 0.08 (4) |
| $d(CH_2)_5$—D-Tyr(Et)VAVP | 1.1 ± 0.2 | 7.81 ± 0.07 (5) | 0.45 ± 0.11 | 8.22 ± 0.12 (4) |
| $d(CH_2)_4$Tyr(Et)VAVP | 2.6 ± 0.4 | 7.43 ± 0.07 (4) | 0.32 ± 0.05 | 8.30 ± 0.07 (4) |
| $d(CH_2)_4$Tyr(Et)VDAVP | 5.0 ± 1.8 | 7.20 ± 0.14 (4) | 0.35 ± 0.06 | 8.30 ± 0.08 (4) |
| $d(CH_2)_4$—D-Tyr(Et)VAVP | 0.72 ± 0.17 | 8.04 ± 0.11 (6) | 0.50 ± 0.07 | 8.14 ± 0.07 (4) |
| $d(CH_2)_4$—D-Tyr(Et)VDAVP | 0.97 ± 0.19 | 7.89 ± 0.11 (5) | 0.79 ± 0.08 | 7.93 ± 0.05 (4) |
| $d(CH_2)_5$—D-Phe$^2$—D-Cy$^6$VAVP | 3.9 ± 0.5 | 7.25 ± 0.06 (4) | 1.9 ± 0.4 | 7.56 ± 0.07 (4) |
| $d(CH_2)_5$Tyr(Et)$^2$—D-Cy$^6$VAVP | 72 | ~6 | 4.4 ± 0.5 | 7.19 ± 0.05 (4) |
| $d(CH_2)_5$—D-Tyr(Et)$^2$—D-Cy$^6$VAVP | 3.3 ± 0.07 | 7.33 ± 0.09 (4) | 0.6 ± 0.04 | 8.06 ± 0.05 (4) |

EXAMPLE 8

[1-($\beta$-Mercapto-$\beta,\beta$-cyclopentamethylenepropionic acid), 2-substituted, 4-valine, 7-substituted]-arginine vasopressin Representative compounds of this group were prepared as in the previous examples, using D-proline instead of proline at the 7-position. Properties of typical compounds were:

(a) $d(CH_2)_5$-D-Tyr(Et)$^2$-D-Pro$^7$-VAVP
$R_f(E)$: 0.12
$R_f(F)$: 0.63

(b) $d(CH_2)_5$-Tyr(Et)$^2$-D-Pro$^7$-VAVP
$R_f(E)$: 0.12
$R_f(F)$: 0.53

Effective doses as antagonists of antidiuretic and vasopressor action of arginine vasopressin were determined as in Example 6. Results were:

| | ED's in nmole/kg | |
|---|---|---|
| | Anti-ADH | Anti-VP |
| $d(CH_2)_5$—D-Tyr(Et)$_2$—D-Pro$^7$—VAVP | 1.6 ± 0.3 | 0.55 ± 0.09 |
| $d(CH_2)_5$Tyr(Et)$^2$—D-Pro$^7$—VAVP | 35 ± 7 | 0.45 ± 0.15 |

These results show that VAVP compounds, containing D-Pro at the 7-position, are active as antagonists of the antidiuretic action of arginine vasopressin.

The preceding examples can be repeated with similar success by substituting the generically or specifically described reactants and/or operating conditions of this invention for those used in the preceding Examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A compound of the formula $$\begin{array}{c} 1 \quad\quad 2\ 3\ \ 4\ \ \ 5\ \ \ 6\ \ \ 7\ 8\ \ 9 \\ CH_2\text{-}CO\text{-}X\text{-}Phe\text{-}Val\text{-}Asn\text{-}Cys\text{-}Pro\text{-}Z\text{-}Gly\text{-}NH_2 \\ | \quad\quad\quad\quad\quad\quad\quad\quad\quad | \\ (CH_2)_4 \quad C \quad\quad\quad\quad\quad\quad\quad\quad | \\ | \quad\quad\quad\quad\quad\quad\quad\quad\quad\quad | \\ S\text{------}S \end{array}$$

wherein X is (D- or L-)Tyr(R), D-Tyr, D-Phe, D-Val, D-Leu, D-Ile, D-Arg, D-Gln, D-Asn, D-NVa, D-Nle, D-Cha, D-Abu, D-Thr or D-Met; R is methyl, ethyl, propyl or butyl and Z is L- or D-Arg.

2. A compound of claim 1, wherein X is (D- or L-)Tyr(R) and R is methyl, ethyl, propyl or butyl.

3. A compound of claim 1, wherein X is D-Tyr(R).

4. A compound of claim 3, wherein R is ethyl.

5. A compound of claim 1, wherein Z is L-Arg.

6. A compound of claim 1, wherein Z is D-Arg.

7. [1-($\beta$-Mercapto-$\beta,\beta$-cyclotetramethylenepropionic acid), 2-D-(O)-ethyltyrosine), 4-valine]-arginine vasopressin, a compound of claim 1.

8. [1-($\beta$-Mercapto-$\beta,\beta$-cyclotetramethylenepropionic acid), 2-D-(O-ethyltyrosine), 4-valine, 8-D-arginine] vasopressin, a compound of claim 1.

9. A method for antagonizing the in vivo response of an animal to the antidiuretic action of an antidiuretic hormone, comprising administering to the animal being treated an amount of a compound of claim 1, in admixture with a physiologically and pharmaceutically acceptable carrier, effective to antagonize the antidiuretic response to the antidiuretic hormone.

10. The method of claim 9, wherein the antidiuretic hormone is arginine vasopressin.

11. The method of claim 9, wherein the compound is administered parenterally.

12. A method for antagonizing the in vivo response of an animal to the antidiuretic action of an antidiuretic hormone, comprising administering to the animal being treated an amount of the compound of claim 7, in admixture with a physiologically and pharmaceutically acceptable carrier, effective to antagonize the antidiuretic response to the antidiuretic hormone.

13. A method for antagonizing the in vivo response of an animal to the antidiuretic action of an antidiuretic hormone, comprising administering to the animal being treated an amount of a compound of claim 8, in admixture with a physiologically and pharmaceutically acceptable carrier, effective to antagonize the antidiuretic response to the antidiuretic hormone.

14. A compound of the formula $$\begin{array}{c} CH_2\text{-CO-X-Phe-Val-Asn-(D-Cys)-Pro-Z-Gly-NH}_2 \\ | \\ (CH_2)_n \quad C \\ | \qquad\qquad\qquad\qquad | \\ S\text{————————————}S \end{array}$$

wherein X is (D- or L-)Tyr(R), D-Tyr, D-Phe, D-Val, D-Leu, D-Ile, D-Arg, D-Gln, D-Asn, D-NVa, D-Nle, D-Cha, D-Abu, D-Thr or D-Met; R is ethyl, methyl, propyl or butyl; n is 4 or 5 and Z is D- or L-Arg.

15. A compound of claim 14, wherein X is (D- or L-)Tyr(R).
16. A compound of claim 14, wherein X is D-Phe.
17. A compound of claim 14, wherein Z is Arg.
18. A compound of claim 14, wherein n is 5.
19. A method for antagonizing the in vivo response of an animal to the antidiuretic action of an antidiuretic hormone, comprising administering to the animal being treated an amount of a compound of claim 14, in admixture with a physiologically and pharmaceutically acceptable carrier, effective to antagonize the antidiuretic response to the antidiuretic hormone.
20. A compound of the formula $$\begin{array}{c} CH_2\text{-CO-X-Phe-Val-Asn-(D- or L-)Cys-Pro-Z'-Gly-NH}_2 \\ | \\ (CH_2)_n \quad C \\ | \qquad\qquad\qquad\qquad | \\ S\text{————————————}S \end{array}$$

wherein X is D-Phe, D-Tyr, (D- or L-)Tyr(R), D-Val, D-Leu, D-Ile, D-Arg, D-Gln, D-Asn, D-NVa, D-Nle, D-Cha, D-Abu, D-Thr or D-Met; R is methyl, ethyl, propyl or butyl; n is 4 or 5 and Z' is (D- or L-)Lys or (D- or L-)Orn.

21. A compound of claim 20, wherein Z is Orn.
22. A compound of claim 20, wherein Z is Lys.
23. A compound of claim 20, wherein X is (D- or L-)Tyr(R).
24. A compound of claim 20, wherein X is D-Ile.
25. A compound of claim 20, wherein n is 5.
26. A method of antagonizing the in vivo response of an animal to the antidiuretic action of an antidiuretic hormone, comprising administering to the animal being treated an amount of a compound of claim 20, in admixture with a physiologically and pharmaceutically acceptable carrier, effective to antagonize the antidiuretic response to the antidiuretic hormone.
27. A compound of the formula $$\begin{array}{c} CH_2\text{-CO-X-Phe-Val-Asn-(D- or L-)Cys-W-Z''-Gly-NH}_2 \\ | \\ (CH_2)_n \quad C \\ | \qquad\qquad\qquad\qquad | \\ S\text{————————————}S \end{array}$$

wherein X is D-Tyr, (D- or L-)Tyr(R), D-Phe, D-Val, D-Leu, D-Ile, D-Arg, D-Gln, D-Asn, D-NVa, D-Nle, D-Cha, D-Abu, D-Thr or D-Met; R is methyl, ethyl, propyl or butyl; W is D-Pro, $\Delta^3$-Pro or HO-Pro; Z" is (D- or L-)Arg, (D- or L-)Orn or (D- or L-)Lys and n is 4 or 5; provided that when X is (D- or L-)Tyr(R) and n is 5, W is HO-Pro or D-Pro and when X is D-Gln or D-Asn and n is 5, W is also Pro.

28. A compound of claim 27, wherein W is $\Delta^3$-Pro.
29. A compound of claim 27, wherein W is D-Pro.
30. A compound of claim 27, wherein X is (D- or L-)Tyr(R).
31. A compound of claim 27, wherein n is 5.
32. A method of antagonizing the in vivo response of an animal to the antidiuretic action of an antidiuretic hormone, comprising administering to the animal being treated an amount of a compound of claim 27, in admixture with a physiologically and pharmaceutically acceptable carrier, effective to antagonize the antidiuretic response to the antidiuretic hormone.

* * * * *

UNITED STATES PATENT AND TRADEMARK OFFICE
CERTIFICATE OF CORRECTION

PATENT NO. : 4,491,577
DATED : January 1, 1985
INVENTOR(S) : Maurice Manning and Wilbur H. Sawyer It is certified that error appears in the above—identified patent and that said Letters Patent is hereby corrected as shown below:

Column 12, line 8, column 13, lines 5 and 30 and column 13, line 16, for that portion of the formula reading:

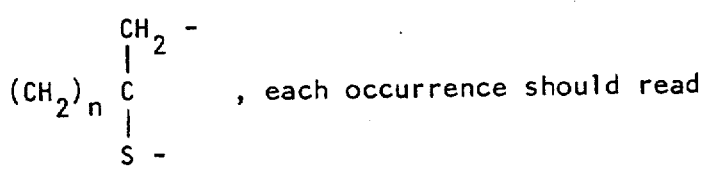, each occurrence should read 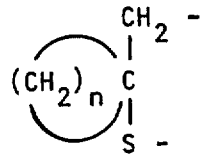

Signed and Sealed this

Twenty-first Day of November, 1989

Attest:

JEFFREY M. SAMUELS

Attesting Officer     Acting Commissioner of Patents and Trademarks